(12) United States Patent
Kato et al.

(10) Patent No.: US 9,433,542 B2
(45) Date of Patent: Sep. 6, 2016

(54) ABSORBENT ARTICLE AND PRODUCTION METHOD THEREOF

(75) Inventors: Nobuyuki Kato, Kanonji (JP); Tatsuya Tamura, Kanonji (JP); Toshihisa Hayashi, Kanonji (JP); Masashi Kitagawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 20 days.

(21) Appl. No.: 14/002,762

(22) PCT Filed: Feb. 27, 2012

(86) PCT No.: PCT/JP2012/055491
§ 371 (c)(1),
(2), (4) Date: Sep. 3, 2013

(87) PCT Pub. No.: WO2012/118214
PCT Pub. Date: Sep. 7, 2012

(65) Prior Publication Data
US 2013/0345656 A1    Dec. 26, 2013

(30) Foreign Application Priority Data

Mar. 2, 2011    (JP) ................................. 2011-044959

(51) Int. Cl.
*A61F 13/475*    (2006.01)
*A61F 13/533*    (2006.01)
(Continued)

(52) U.S. Cl.
CPC ....... *A61F 13/537* (2013.01); *A61F 13/15617* (2013.01); *A61F 13/15731* (2013.01);
(Continued)

(58) Field of Classification Search
CPC ............... A61F 13/15731; A61F 13/4704; A61F 13/4756; A61F 13/535; A61F 13/539; A61F 2013/53734; A61F 2013/53739; A61F 13/5126; A61F 2013/15373; A61F 2013/15382; A61F 2013/15495; A61F 13/15707; A61F 13/49473; A61F 2013/51078; A61F 13/51104
USPC .......................... D24/125; 604/379, 380, 383
See application file for complete search history.

(56) References Cited

U.S. PATENT DOCUMENTS

| | | |
|---|---|---|
| 2004/0243082 A1 | 12/2004 | Kinoshita et al. |
| 2006/0189954 A1 | 8/2006 | Kudo et al. |
| 2011/0319851 A1* | 12/2011 | Kudo et al. ................... 604/380 |

FOREIGN PATENT DOCUMENTS

| | | |
|---|---|---|
| EP | 2281536 A1 | 2/2011 |
| JP | 04064356 A | 2/1992 |

(Continued)

OTHER PUBLICATIONS

Corresponding International Application No. PCT/JP2012/055491 Search Report dated May 22, 2012.

*Primary Examiner* — Peter S Vasat
(74) *Attorney, Agent, or Firm* — Hauptman Ham, LLP

(57) ABSTRACT

The absorbent article of the present invention comprises: a liquid-pervious surface sheet, a liquid-impervious backside sheet provided at the position opposing said surface sheet, and an absorption body provided between said surface sheet and said backside sheet, wherein the absorbent article comprises an endless compressed groove, surrounding a central part of said absorbent article, which is formed in said surface sheet and said absorption body in the thickness direction, and a plurality of concave parts, provided inside and outside said compressed groove, which are formed in said surface sheet and said absorption body in the thickness direction, and an uncompressed region bordering inner and outer edges of the compressed groove, wherein the closest distance between said compressed groove and the nearest concave parts is greater than the distance between adjacent ones of those same concave parts.

25 Claims, 12 Drawing Sheets

(51) Int. Cl.
*A61F 13/537* (2006.01)
*A61F 13/15* (2006.01)
*A61F 13/535* (2006.01)
*A61F 13/539* (2006.01)
*A61F 13/47* (2006.01)

(52) U.S. Cl.
CPC ....... *A61F13/4704* (2013.01); *A61F 13/4756* (2013.01); *A61F 13/535* (2013.01); *A61F 13/539* (2013.01); *Y10T 156/1041* (2015.01)

(56) References Cited

FOREIGN PATENT DOCUMENTS

| | | |
|---|---|---|
| JP | 2004229767 A | 8/2004 |
| JP | 2004298411 A | 10/2004 |
| JP | 2005096461 A | 4/2005 |
| JP | 2006230596 A | 9/2006 |
| JP | 2010148708 A | 7/2010 |

* cited by examiner (a)

(b)

(a)

(b)

(a)

(b)

(a)

(b)

(a)

(b)

(c)

(a)

(b)

(a)

(b)

ABSORBENT ARTICLE AND PRODUCTION METHOD THEREOF

RELATED APPLICATIONS

The present application is a National Phase of International Application Number PCT/JP2012/055491, filed Feb. 27, 2012, and claims priority from Japanese Application Number 2011-044959, filed Mar. 2, 2011.

TECHNICAL FIELD

The present disclosure relates to an absorbent.

BACKGROUND ART

An absorbent article comprising a liquid-permeable sheet and an absorption body with a compressed groove disposed at least in longitudinal edge parts on both sides of the central region of the absorption body and a plurality of point-like compressed parts disposed with a spacing from one another, is disclosed in Patent Literature 1. The compressed groove integrates the liquid-permeable sheet with the absorption body and also blocks lateral spreading of any liquid excrement, such as menstrual blood and urine. The point-like compressed parts of this absorbent article can control the movement of the material of the absorption body so that the material is uniformly maintained in the entire absorption body, thereby resisting twisting of the absorbent article.

CITATION LIST

Patent Literature

[Patent Literature 1] Kokai (Japanese Unexamined Patent Publication) No. 2010-148708

SUMMARY OF THE INVENTION

Technical Problem

The inventor(s) has noted that with an arrangement as described above, the body fluid discharged in the central part of the absorbent article can sometimes pass across the compressed groove and reach side parts of the absorbent article. For example, depending on the lifestyle or use, the wearer may not be able to freely replace the absorbent article, such as sanitary napkin. In such a case, the wearer may sit or move while wearing the absorbent article for 6 hours or more hours, and therefore, the body fluid of the wearer may reach the side part of the absorbent article. An object of the present invention is to provide an absorbent article which has an improved resistance to body fluids of the wearer diffusing to the side part of the absorbent article, even when the wearer moves while wearing the absorbent article for a long time, i.e., the liquid leakage preventing performance is more enhanced, and a production method for such an article.

Solution to Problem

The present invention employs the following configurations so as to attain the above-described object.

A first aspect of the present invention provides an absorbent article comprising a liquid-pervious surface sheet, a liquid-impervious backside sheet provided at the position opposing the surface sheet, and an absorption body provided between the surface sheet and the backside sheet, wherein the absorbent article comprises a continuous oval like or nearly circular first compressed groove surrounding the central part of the absorbent article, which is formed by compressing the surface sheet and the absorption body in the thickness direction, and a plurality of concave parts provided inside and outside the first compressed groove, which are formed by compressing the surface sheet and the absorption body in the thickness direction by pin embossing, are disposed, and an uncompressed region is present inside, outside and along the first compressed groove, and the distance between the first compressed groove and the concave part is larger than the distance between the concave part and a concave part adjacent to the concave part.

According to a second aspect of the invention there is provided a method for producing an absorbent article of the present invention comprises a step of producing an absorption body, a step of covering the absorption body with a surface sheet, and a forming step of passing the absorption body covered with the surface sheet between an upper roller equipped with a convex part for forming a compressed groove and a pin for pin embossing and a lower roller located to face the upper roller, thereby forming a compressed groove created resulting from compression of the surface sheet and the absorption body in the thickness direction and a plurality of concave parts created resulting from compression of the surface sheet and the absorption body in the thickness direction by pin embossing.

Advantageous Effects of the Invention

According to the present invention, an absorbent article that has improved liquid leakage preventing performance, and a production method thereof can be obtained.

DESCRIPTION OF EMBODIMENTS

Figure 1:
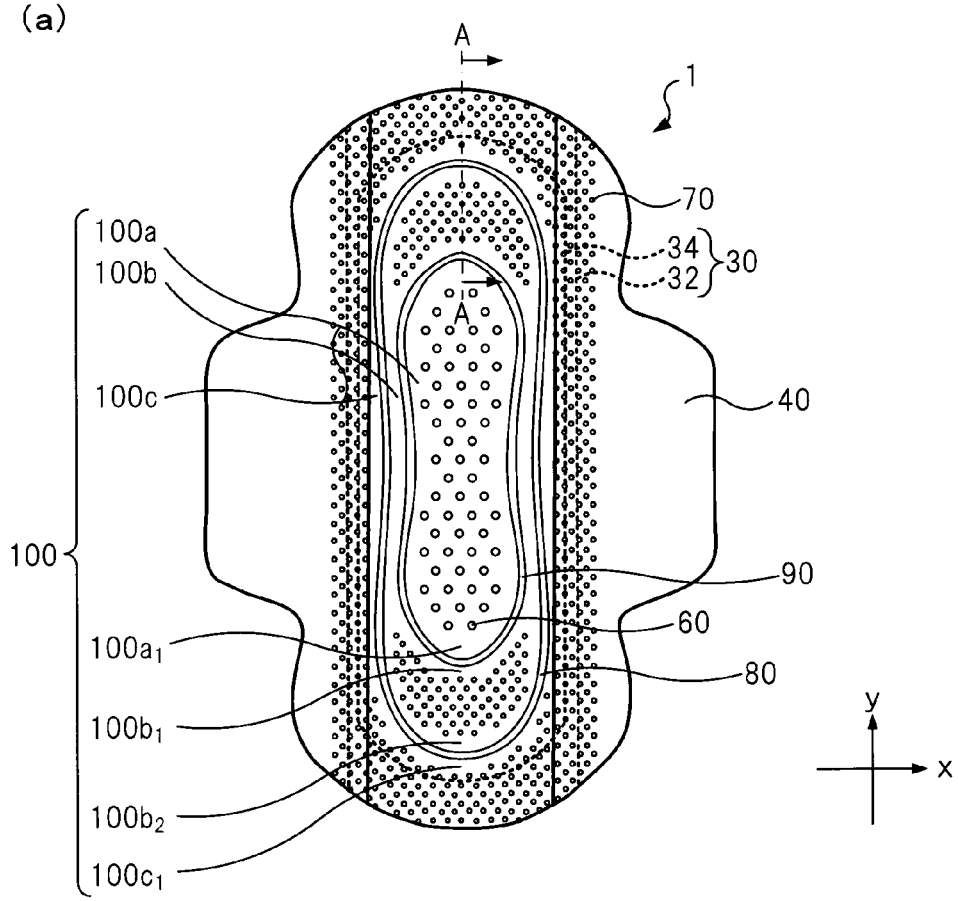
FIG. 1 is a view for explaining the absorbent article in one or more embodiments of the present invention.
Figure 1:
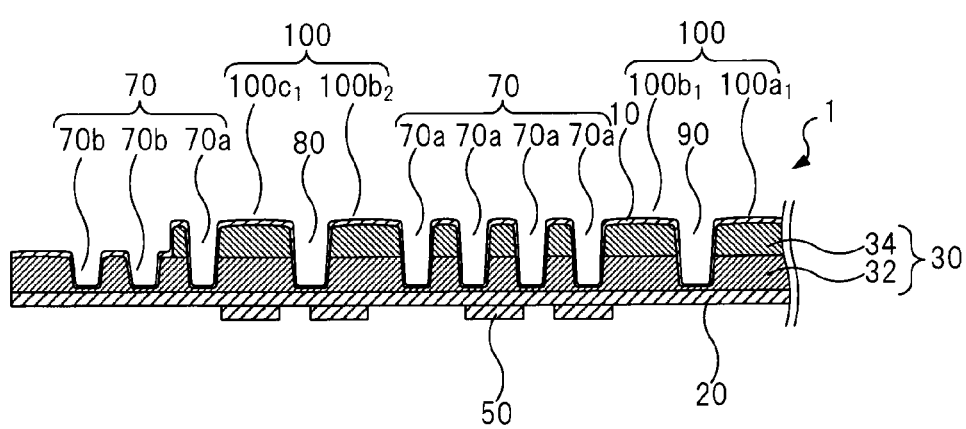

An absorbent article in some embodiments of the present invention is described below by referring to the drawings. The absorbent article in one or more embodiments of the present invention is a thin sanitary napkin.

FIG. 1 is a view for explaining an absorbent article 1 in one or more embodiments of the present invention. FIG. 1(a) is a plan view of the absorbent article 1, and FIG. 1(b) is a view showing the A-A cross-section of FIG. 1(a). The absorbent article 1 comprises a liquid-pervious surface sheet 10, a liquid-impervious backside sheet 20 opposite to the surface sheet 10, an absorption body 30 provided between the surface sheet 10 and the backside sheet, and a side sheet 40 provided on both widthwise sides of the surface sheet 10 and protruding in the width direction. In a modified embodiment, the side sheet does not protrude in the width direction. A pressure-sensitive adhesive part 50 is provided on a non-skin-facing side of the backside sheet 20 which further has a skin-facing side facing the surface sheet 10.

The absorption body 30 includes an air-laid layer 32 formed by joining fibers with a binder. The absorbent body also includes a comminuted pulp layer 34. The air-laid layer 32 is provided on the backside sheet side (or non-skin-facing side) of the absorption body 30, and the comminuted pulp layer 34 is provided on the surface sheet side (or skin-facing side) of the absorption body 30. In the case of a thin absorbent article, the basis weight of the entire absorption body 30 is preferably from 40 to 300 g/m$^2$. The basis weight of the air-laid layer 32 is preferably from 30 to 100 g/m$^2$.

Each of the surface sheet 10 and the absorption body 30 has a plurality of concave parts 60 and 70 extending from the surface sheet 10 to the inside of the absorption body 30. These concave parts 60 and 70 can be formed by being compressed in the thickness direction by pin embossing. Compressed grooves 80 and 90 extend from the surface sheet 10 to the inside of the absorption body 30. These are formed from compression in the thickness direction. Each of the compressed grooves 80 and 90 is endless and encloses a central part of the absorbent article 1. The compressed grooves 80 and 90 are shown as continuous grooves; however they could alternatively be intermittently broken. That is, each of the compressed grooves 80 and 90 may have a discontinuous oval like or nearly circular shape. However, the body fluid may diffuse by passing through the broken portion of the compressed groove and therefore the compressed grooves 80 and 90 are preferably continuous. In the context of the present application, "pin embossing" means embossing using pins provided on a roller. In the Figures, the absorbent article 1 has a transverse width direction indicated by the x-axis and has a longitudinal direction indicated by the y-axis. The term "uncompressed regions" means regions that have not been compressed or regions that are compressed by an insignificant amount relative to other regions. It does not exclude the regions being slightly compressed as a result of a uniform compression being applied to the whole article, or a substrate from which the article is made, during a manufacturing process.

The surface sheet 10 is a sheet for coming into contact with the wearer's skin when the absorbent article is worn. For the surface sheet 10, a nonwoven fabric is often used, but it could be a woven fabric as long as the sheet capable of passing a liquid. For example, a woven fabric, a perforated plastic sheet or a mesh sheet may be used for the surface sheet 10. For the nonwoven fabric used as the surface sheet 10, a natural fiber or a chemical fiber may be used. Examples of the natural fiber used for the surface sheet 10 include a cellulose such as comminuted pulp and cotton. Examples of a chemical fiber used for the surface sheet 10 include a regenerated cellulose such as rayon and fibril rayon, a semisynthetic cellulose such as acetate and triacetate, a thermoplastic hydrophobic chemical fiber, and a thermoplastic hydrophobic chemical fiber subjected to a hydrophilization treatment. Examples of the thermoplastic hydrophobic chemical fiber include a single fiber such as polyethylene (PE), polypropylene (PP) and polyethylene terephthalate (PET), a fiber obtained by graft copolymerization of polyethylene and polypropylene, and a composite fiber such as fiber having a core-sheath structure.

As the method for producing a nonwoven fabric used for the surface sheet 10, a dry process (for example, card, spunbond, meltblown and air-laid) or a wet process may be used, or both a dry process and a wet process may be also combined. Furthermore, the nonwoven fabric used for the surface sheet 10 may be produced by a method such as thermal bonding, needle punching and chemical bonding. However, the method for producing the nonwoven fabric is not limited to the methods above, and the nonwoven fabric may be produced by other methods.

As the nonwoven fabric used for the surface sheet 10, for example, a spunlace formed in a sheet form by a hydroentangling method may be also used. Furthermore, as the nonwoven fabric used for the surface sheet 10, a nonwoven fabric imparted with unevenness on the upper layer side of the nonwoven fabric, or an uneven nonwoven fabric obtained by applying an air during web formation and thereby creating basis weight unevenness in the nonwoven fabric, may be also used. In the case of forming unevenness on the nonwoven fabric surface, diffusion of a body fluid along the surface of the surface sheet 10 before passing through the surface sheet 10 can be reduced.

The backside sheet 20 is a sheet for preventing a body fluid discharged by the wearer and absorbed in the absorption body 30 from leaking outside. The backside sheet 20 may, for example, be a film mainly comprising polyethylene, polypropylene or the like, an air-permeable resin film, or a sheet obtained by joining an air-permeable resin film with a nonwoven fabric such as spunbond and spunlace, may be used. The backside sheet 20 preferably has flexibility sufficient to give no uncomfortable feeling to the wearer during wearing.

The air-laid layer 32 of the absorption body 30 comprises an air-laid nonwoven fabric. The air-laid nonwoven fabric is produced, for example, by dispersing a mixture of a hydrophilic fiber and a thermoplastic resin fiber in air, passing the mixture through a woven metal screen having pores to fall on a wire running under the screen, spraying a water-soluble binder, and applying a heat treatment to thermally weld the thermoplastic resin fiber and the hydrophilic fiber. Incidentally, the thermoplastic resin fiber and the hydrophilic fiber may be thermally welded by thermally fusing the thermoplastic resin fiber surface to the hydrophilic fiber without using a water-soluble binder. In this case, the surface of the thermoplastic resin fiber functions as a binder for thermally welding the thermoplastic resin fiber and the hydrophilic fiber.

For example, a nonwoven fabric obtained by bonding pulp as the hydrophilic fiber and a composite thermoplastic resin fiber (2.2 dtex, fiber length: 5 mm) with the core being PET (polyethylene terephthalate) and the sheath being PE (polyethylene), through spraying of a vinyl alcohol-based emulsion adhesive and heat treatment may be used as air-laid nonwoven fabric.

As the hydrophilic fiber, one member or a mixture of two or more members selected from wood pulp, rayon, acetate rayon, a natural cellulose fiber other than pulp, mercerized pulp and crosslinked pulp is used. Also, as the thermally weldable thermoplastic resin fiber, a composite thermoplastic resin fiber with the core being PP (polypropylene) and the sheath being PE, or a single fiber of PE, PP or PET may be used, in addition to the above-described composite thermoplastic resin fiber.

The comminuted pulp layer 34 of the absorption body 30 is a layer mainly containing comminuted pulp or a layer composed exclusively of comminuted pulp. For example, the comminuted pulp is produced by comminuting a pulp sheet by a comminutor. The comminuted pulps are not joined to each other through an adhesive or the like.

The absorption body 30 may have other layers between the air-laid layer 32 and the comminuted pulp layer 34. Also, the absorption body 30 may have other layers on the non-skin-facing side of the air-laid layer 32 opposite from the comminuted pulp layer 34.

The air-laid layer 32 is provided towards the backside sheet side of the absorption body 30, and the comminuted pulp layer 34 is provided towards the surface sheet side of the absorption body 30, whereby an absorption body 30 allowing a body fluid to be preferentially absorbed in the absorption-inhibiting binder-free comminuted pulp layer on the surface sheet side and enjoying the durability benefit of the air-laid sheet obtained by bonding pulp fibers to each other with a binder can be formed.

The absorption body may comprise a comminuted pulp layer on the surface sheet 10 side and an absorbent material layer other than an air-laid layer. Also, the absorption body may comprise an absorbent material other than comminuted pulp.

The planewise region (in plan view) of the comminuted pulp layer 34 is encompassed in the planewise region of the air-laid layer 32, whereby planewise diffusion of a body fluid of the wearer can be constrained on the center side of the absorbent article 1.

The surface sheet 10 is joined with the absorption body 30 by using, for example, a hot-melt adhesive. Examples of the coating pattern of the hot-melt adhesive on the surface sheet 10 or the absorption body 30 include a parallel line pattern where parallel lines are widthwise parallelly arranged with a predetermined spacing and longitudinally extend, a belt pattern where belts are widthwise parallelly arranged and longitudinally extend, a wave pattern where wavy lines oscillating in the width direction and extending in the longitudinal direction are widthwise parallelly arranged, and a spiral pattern where longitudinally extending spirals are arranged in the width direction. The basis weight of the adhesive coated is preferably from 1 to 10 g/m². Within this range, the hot-melt adhesive is entirely distributed and at the same time, the absorbent article 1 can be reduced in the hard touch due to the presence of a hot-melt adhesive, as a result, the feel during use of the absorbent article 1 is improved.

The side sheet 40 is a sheet for preventing a body fluid of the wearer from flowing in the width direction of the absorbent article 1 and leaking outside. As the side sheet 40, for example, the same material as the surface sheet 10 is used. Also, for preventing a body fluid of the wearer from flowing over the side sheet 40, the material for the side sheet 40 preferably has hydrophobicity or water repellency. For example, a spunbond nonwoven fabric or a spun-bonded/melt-blown/spun-bonded (SMS) nonwoven fabric can be used for the side sheet 40. The side sheet 40 comes into contact with skin of the wearer and therefore, an air-through nonwoven fabric is preferably used so as to reduce the rubbing irritation of the skin.

The circumferential edges of the surface sheet 10, the backside sheet 20 and the side sheet 40 may be joined by using any one method of heat embossing, ultrasonic processing and hot-melt adhesive or by combining a plurality of methods.

Concave parts 60 and 70 extending from the surface sheet 10 to the absorption body 30 may be formed by pin embossing, as defined above. The concave parts 60 and 70 are arranged in a zigzag manner, but they may be distributed in another pattern. The planewise shape of openings of the concave parts 60 and 70 is a circular shape (in plan view). Incidentally, the plurality of concave parts may have two or more different planewise shapes, and therefore the rigidity and thickness of the absorption body 30 of the absorbent article 1, in which concave parts are formed by embossing, can be further controlled. For example, while the concave parts 60 in the central part of the absorbent article have a planewise square shape, the concave parts 70 in the peripheral part of the absorbent article may have a planewise circular shape. The planewise shape of the concave parts of the absorbent article is not limited to a circular or square shape and may be, for example, another polygonal shape such as rectangle or triangle, a star shape, or an elliptical shape. In this case, the planewise diameter of a concave part is the diameter of the smallest circle that completely contains the opening of the concave part. Also, the plurality of concave parts may include concave parts having at least two different planewise sizes (diameters) and/or concave parts having at least two different planewise shapes. Thanks to this configuration, the thickness and density distribution of the entire absorption body of the absorbent article, in which concave parts are formed by embossing, can be further controlled and in turn, diffusion of a body fluid discharged from the wearer to the absorption body can be further controlled.

In the case where the absorbent article 1 is less than 4 mm thick, the distance in the planar direction (xy direction) between two adjacent concave parts 60 or between two adjacent concave parts 70 is preferably 3 mm or more, more preferably from 3 to 20 mm. If the planewise distance between two adjacent concave parts 60 or between two adjacent concave parts 70 is less than 3 mm, the compression in the portion between the two adjacent concave parts 60 or 70 of the absorption body 30 may be too strong and this may weaken the cushioning property of the absorbent article 1 and harden the absorbent article 1. If the planewise distance between two adjacent concave parts 60 or between two adjacent concave parts 70 exceeds 20 mm, compression in the portion between two adjacent concave parts 60 or 70 of the absorption body 30 is excessively weak and a body fluid of the wearer may be constrained from being sucked in the portion between the two adjacent concave parts 60 or 70 of the absorption body 30. Also, in this case, the comminuted pulp between the concave parts 60 or 70 may be unevenly distributed, and the absorption body 30 may be twisted.

In the case where the absorbent article 1 is less than 4 mm thick, the planewise diameter of the concave parts 60 and 70 is preferably from 0.5 to 4.0 mm. If the planewise diameter of the concave parts 60 and 70 is less than 0.5 mm, the comminuted pulp layer 34 may not be sufficiently fixed to the air-laid layer 32 by the concave parts 60 and 70, and the absorbent article 1 may not be prevented from twisting. If the planewise diameter of the concave parts 60 and 70 exceeds 4.0 mm, the rigid portion contacting with the skin is increased and the wearer may perceive the absorbent article 1 to be hard when a body pressure is imposed thereon.

To provide the overall absorbent article 1 with a sufficiently high certain level of flexibility and durability to cause no distortion or the like, the ratio of the total planewise area of the concave parts 60 and 70 is preferably from 3 to 30%, more preferably from 5 to 10%, based on the total planewise area of the absorbent article 1.

As shown in FIG. 1, the concave parts 60 and 70 provided in the absorbent article 1 include concave parts having two different planewise sizes. In particular, the planewise size of the concave parts 60 in the central part which is substantially the center in the longitudinal direction and the width direction of the absorbent article 1, is preferably larger than the planewise size of the concave parts 70 in the peripheral part around the central part. Also, the number of concave parts 60 per unit area in the central part of the absorbent article 1 is preferably smaller than the number of concave parts 70 per unit area in the peripheral part around the central part.

Figure 2:
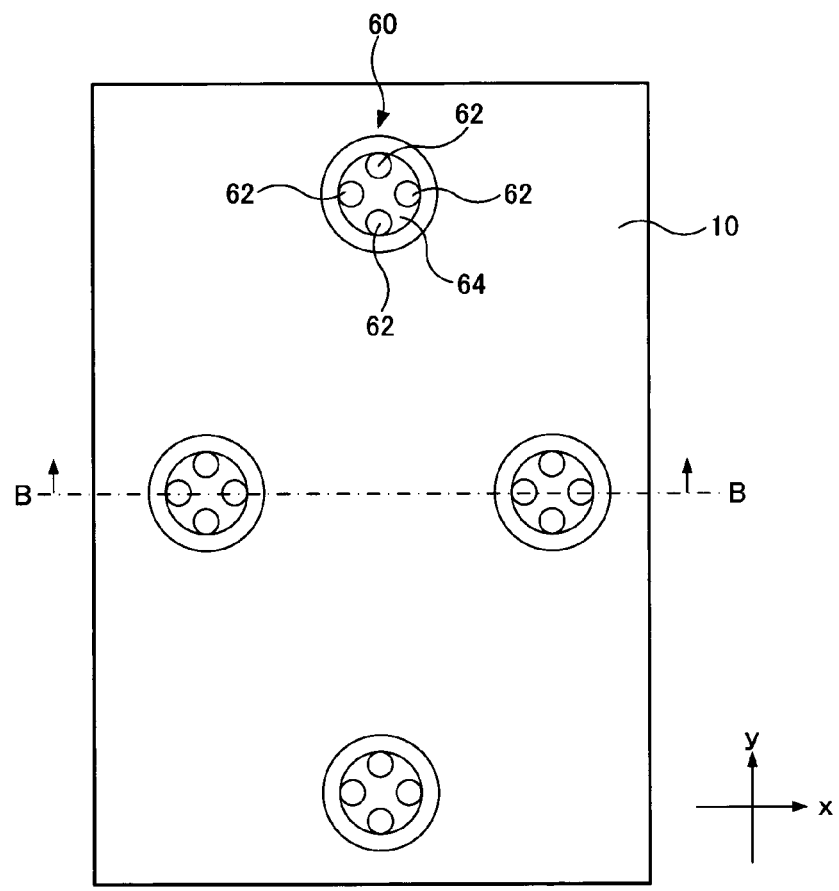
FIG. 2 is a view for explaining the concave parts in the central part of the absorbent article in one or more embodiments of the present invention.
Figure 2:
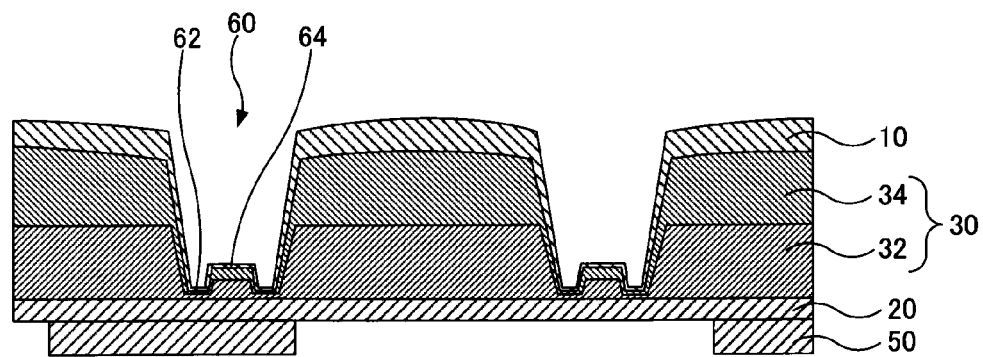

FIG. 2(a) is a plan view of the concave part 60 in the central part of the absorbent article 1, and FIG. 2(b) is a B-B cross-sectional view of FIG. 2(a). As shown in FIG. 2, the concave part 60 in the central part of the absorbent article 1 includes a high compression area 62 and a low compression area 64 differing in the depth in the thickness direction. The depth in the thickness direction of the high compression area 62 is larger than the depth in the thickness direction of the low compression area 64. Four high compression areas 62 are provided in one concave part 60. The planewise shape of the high compression part 62 is a circular shape. Incidentally, a high compression area and a low compression area may be provided also in the concave part 70 in the peripheral part of the absorbent article 1. The planewise shape of the high compression area 62 is not limited to a circular shape and may be, for example, another polygonal shape such as a rectangle or triangle, or a star shape. Furthermore, the number of four high compression areas provided in one concave part is not limited to 4 and may be 1, 2, 3 or 5 or more.

As shown in FIG. 2, a surface sheet 10 is present at the bottom of the concave part 60 in the central part of the absorbent article 1, but the surface sheet 10 may not be present at the bottom of the concave part 60. However, in order to prevent the pulp in the absorption body 30 from escaping, the surface sheet 10 is preferably present at the bottom of the concave part 60. Furthermore, the surface sheet 10 may or may not be present at the bottom of the concave part 70 in the peripheral part of the absorbent article 1 but for the same reason, the surface sheet 10 is preferably present at the bottom of the concave part 70.

The compressed grooves 80 and 90 formed on the surface sheet 10 and the absorption body 30 are created, as described above, by compressing the surface sheet and the absorption body in the thickness direction. The compressed grooves 80 and 90 have a continuous oval like or nearly circular shape surrounding the central part of the absorbent article 1. Incidentally, in the absorbent article 1 shown in FIG. 1, two compressed grooves 80 and 90 are provided, but only one compressed groove may be provided in the absorbent article. Alternatively, three or more compressed grooves may be provided in the absorbent article. In this case, the central part of the absorbent article 1 is surrounded by three or more compressed grooves.

The first compressed groove 80 on the outer side encompasses the second compressed groove 90 in the inside thereof. The closest distance between the compressed groove 80 and the respective concave parts 70 present inside and outside the compressed groove 80 is preferably larger than the distance between adjacent concave parts 70. The closest distance between the compressed groove 90 and the respective concave parts 60 present inside the compressed groove 90 is preferably larger than the distance between adjacent concave parts 60. This configuration results in a region 100 bordering the compressed groove 80 or 90 in which no concave part 60 or 70 is provided. Hereinafter, this region is referred to as an uncompressed region 100. The longitudinal end part of the comminuted pulp layer 34 is present on the outer side relative to both the first compressed groove 80 and the uncompressed region 100 provided outside the first compressed groove 80, and therefore, due to this configuration, the body fluid of the wearer can be prevented from diffusing to the end of the absorbent article 1. Also, due to the configuration above, the absorbent article 1 is unlikely to be twisted even if the absorbent article 1 has been worn for a long time, so that the body fluid of the wearer can be prevented from diffusing to the side part of the absorbent article 1 due to twisting of the absorbent article 1. For example, depending on the lifestyle or use, the wearer cannot freely replace the absorbent article, such as sanitary napkin, in some cases. In such a case, the wearer often sits or moves while wearing the absorbent article for 6 hours or more. When the absorbent article is worn for 6 hours or more, twisting of the absorbent article may occur and therefore, the absorbent article may be twisted to allow the body fluid of the wearer to reach the side part of the absorbent article. However, in the absorbent article in one or more embodiments of the present invention, the longitudinal end part of the comminuted pulp layer 34 is present on the outer side relative to both the first compressed groove 80 and the uncompressed region 100 provided outside the first compressed groove 80, and therefore, the absorbent article is hardly twisted even when the wearer moves and the absorbent article has been worn for a long time, so that the body fluid of the wearer can be prevented from diffusing to the side part of the absorbent article even when the absorbent article has been worn for a long time.

The body fluid of the wearer is discharged first in the central part of the absorbent article 1. In the absorption body 30 corresponding to the central part of the absorbent article 1, the concave parts 60 are formed. A liquid is sucked preferentially in the high-density portion of the absorption body. Accordingly, the body fluid of the wearer accumulates preferentially in a high-density portion having formed therein the concave parts 60 of the absorption body 30 than in the portion of the uncompressed region $100a_1$ of the absorption body 30, whereby the body fluid of the wearer can be prevented from diffusing outside of the central part or thus to the end of the absorbent article 1. When the amount of the body fluid of the wearer is increased, it may not be possible to retain all the body fluid in the higher density central part having formed therein the concave parts 60 of the absorption body 30. In this case, the body fluid of the wearer passes through the portion of the uncompressed region $100a_1$ of the absorption body 30 and reaches the portion having formed therein the second compressed groove 90 of the absorption body 30. The portion of the absorption body 30 having the second compressed groove 90 formed therein is a high-density portion of the absorption body 30 and therefore, the body fluid of the wearer accumulates preferentially in the portion having formed therein the second compressed groove 90 of the absorption body 30. When the amount of the body fluid further increases, additional body fluid accumulates in a portion having formed therein concave parts between the second compressed groove 90 and the first compressed groove 80 in preference to an uncompressed region $100b_2$ bordering the inside edge of the first compressed groove 80. When the amount of the body fluid is still further increased, the body fluid accumulates preferentially in the portion having formed therein the first compressed groove 80 than in the portion of the uncompressed region $100c_1$ bordering the outside edge of the first compressed groove 80. When the amount of the body fluid is yet still further increased, the body fluid will second additionally accumulate in the portion of the absorption body outside the first groove having concave part 70a in a region of the absorption body comprising both the comminuted pulp layer 34 and the air-laid layer 32 before additionally accumulating in a region of the absorption body outside the first groove 80 having concave parts 70b comprising the air-laid layer 32. In this way, the body fluid of the wearer can be deterred from diffusing to the end of the absorbent article 1, through several stages dependent on the amount of body fluid.

In order to effectively prevent the body fluid of the wearer from diffusing to the end of the absorbent article 1, the difference between the density in the portion of the uncompressed region 100 of the absorption body 30 and the density in the portion having formed therein the compressed groove 80 or 90 or the concave part 60 or 70 of the absorption body 30 is preferably larger. In particular, the density of the uncompressed region 100 is preferably ¼ or less of the density of the compressed groove 80 or 90 or the concave part 60 or 70. Accordingly, the thickness in the portion of the uncompressed region 100 of the absorption body 30 is preferably 4 times or more of the thickness in the portion having formed therein the compressed groove 80 or 90 or the concave part 60 or 70 of the absorption body 30.

In the absorbent article 1, the width of the uncompressed regions 100 present on the width direction side of the absorbent article 1 is larger than the width of the uncompressed regions 100 present on the longitudinal direction side of the absorbent article 1. The width of the uncompressed regions 100 is the dimension of the uncompressed regions 100, in the width direction of the compressed grooves 80 and 90, that is, in the direction perpendicular to the compressed grooves 80 and 90. When the width of the uncompressed regions 100 is increased, the thickness in the portion of the uncompressed region 100 of the absorption body 30 is usually increased and the density in the portion of the uncompressed regions 100 of the absorption body 30 is usually decreased. In turn, the difference between the density in the portion having formed therein the concave parts 60 and 70 of the absorption body, and the density of the uncompressed region 100 of the absorption body becomes large and therefore, any body fluid from the wearer accumulates more in the portion having formed therein the concave parts 60 and 70 of the absorption body, than in the portion of the uncompressed region 100 of the absorption body, whereby the effect of preventing the body fluid of the wearer from diffusing to the end of the absorbent article 1 is increased. Meanwhile, in the absorbent article 1, the body fluid of the wearer may be more likely to leak in the width direction more than in the longitudinal direction. When the width of the uncompressed regions 100 present on the widthwise side of the absorbent article 1 is set to be larger than the width of the uncompressed regions 100 present on the longitudinal side of the absorbent article 1, the effect of preventing the body fluid of the wearer from diffusing to the end of the absorbent article 1 can be made greater in the width direction than in the longitudinal direction of the absorbent article 1.

Specifically, the width of the uncompressed regions 100 is preferably from 3 to 10 mm. If the width of the uncompressed regions 100 is less than 3 mm, the density of the absorption body 30 in the uncompressed regions 100 may not be sufficiently decreased, reducing the effect of preventing diffusion of the body fluid. Also, if the width of the uncompressed regions 100 exceeds 10 mm, the difference between the density in the uncompressed region 100 of the absorption body 30 and the density in the region where the concave parts 60 and 70 are formed may not be sufficiently increased, reducing the effect of preventing the diffusion of the body fluid, or the area of the region where the density of the absorption body 30 becomes high due to formation of the concave parts 60 and 70 may be decreased, allowing a small region for preferential accumulation of the body fluid.

With respect to the compressed grooves 80 and 90 and the concave parts 70 present outside the compressed grooves 80 and 90, the closest distance between the compressed groove 80 or 90 and the concave part 70 present outside the compressed groove 80 or 90 is preferably larger than the distance between the two adjacent concave parts 70, and therefore due to this configuration, the body fluid of the wearer can be prevented from diffusing to the end of the absorbent article 1.

When the amount of the body fluid of the wearer is increased, the body fluid may not be kept accumulating only in the portion having formed therein the concave parts 60 of the absorption body 30. In this case, the body fluid of the wearer passes through the portion of the uncompressed region 100 bordering the inner edge of the second compressed groove 90 and reaches the portion of the absorption body 30 having formed therein the second compressed groove 90. The portion having formed therein the second compressed groove 90 of the absorption body 30 is a high-density portion of the absorption body 30 and therefore, the body fluid of the wearer accumulates preferentially in the portion having formed therein the second compressed groove 90 of the absorption body 30. When an uncompressed region 100 is present outside the second compressed groove 90, the difference between the density in the second compressed groove 90 portion of the absorption body 30 and the density in the portion outside the second compressed groove 90 of the absorption body 30 becomes large, and the body fluid of the wearer is more likely to accumulate in the second compressed groove 90 of the absorption body 30, which further increases the effect of preventing the body fluid of the wearer from diffusing to the end of the absorbent article 1.

Specifically, the width of the uncompressed region 100 outside the compressed grooves 80 and 90 is preferably from 5 to 10 mm. If the width of the uncompressed region 100 is less than 5 mm, the density of the absorption body 30 in the uncompressed region 100 may not be sufficiently decreased, reducing the effect of preventing diffusion of the body fluid. Also, if the width of the uncompressed region 100 exceeds 10 mm, the difference between the density in the uncompressed region 100 of the absorption body 30 and the density in the region where the concave parts 60 and 70 are formed may not be sufficiently increased, reducing the effect of preventing the diffusion of the body fluid, or the area of the region where the density of the absorption body 30 becomes high due to formation of the concave parts 60 and 70 may be decreased, allowing a small region for preferential accumulation of the body fluid.

The width of the uncompressed region 100 present outside the compressed grooves 80 and 90 is preferably larger than the width of the uncompressed region 100 present inside the compressed grooves 80 and 90, and therefore due to this configuration, the body fluid of the wearer is more likely to accumulate on the inside of the compressed grooves 80 and 90, than on the outside of the compressed grooves 80 and 90, whereby the body fluid of the wearer can be constrained from passing through the compressed grooves 80 and 90 of the absorption body 30.

Incidentally, the concave parts may be provided only inside the compressed groove, or the concave parts may be provided only outside the compressed groove. However, for enhancing the liquid leakage preventing performance, the concave parts are preferably provided both inside and outside the compressed groove.

The absorbent article 1 preferably has a continuous oval like or nearly circular second compressed groove 90 surrounding the central part of the absorbent article 1, formed by compressing the surface sheet 10 and the absorption body 30 in the thickness direction, and provided inside the first compressed groove 80. In this configuration, the body fluid of the wearer discharged in the central part must pass through two compressed grooves 80 and 90 to reach the end of the absorbent article 1 and therefore, the effect of preventing the body fluid of the wearer from diffusing to the end of the absorbent article 1 is more increased. The plurality of concave parts 70 are shown also disposed between the outer first compressed groove 80 and the inner second compressed groove 90 with uncompressed regions 100 present between the outer first compressed groove 80 and the inner second compressed groove 90. As a result, the body fluid of the wearer is more likely to accumulate in the portion having the plurality of concave parts 70 of the absorption body 30, the portion having the outer first compressed groove 80 of the absorption body 30, and the portion having the inner second compressed groove 90 of the absorption body 30, and therefore, the effect of preventing the body fluid of the wearer from diffusing to the end of the absorbent article 1 is further increased.

The concave parts 60 and 70 may not be provided between the outer first compressed groove 80 and the inner second compressed groove 90 on the widthwise side of the absorbent article 1. That is, only the uncompressed region 100 may be allowed to be present between the outer first compressed groove 80 and the inner second compressed groove 90 on the widthwise side of the absorbent article 1. As a result, the width of the uncompressed region 100 between the outer first compressed groove 80 and the inner second compressed groove 90 on the widthwise side of the absorbent article 1 can be made large and therefore, the difference between the density in the portion having the compressed groove 80 or 90 of the absorption body 30 and the density in the portion of the uncompressed region 100 of the absorption body 30 can be increased. In turn, the body fluid of the wearer is more likely to accumulate in the portion having the outer first compressed groove 80 of the absorption body 30 and the portion having the inner second compressed groove 90 of the absorption body 30, and this increases the effect of preventing the body fluid of the wearer from diffusing to the end of the absorbent article 1.

The pressure-sensitive adhesive part 50 is a pressure-sensitive adhesive layer for fixing the absorbent article 1 to the underwear coming into contact with the non-skin-contact surface of the backside sheet 20. The pressure-sensitive adhesive part 50 is formed by coating a pressure-sensitive adhesive on the non-skin-contact surface of the backside sheet 20 or by coating a pressure-sensitive adhesive on a packaging sheet with the entire surface being release-treated and then transferring the coated pressure-sensitive adhesive to the non-skin-contact surface of the backside sheet 20. Incidentally, it is also possible to transfer an adhesive by a method of coating an adhesive on a separate release paper other than the packaging sheet. The planewise shape of the adhesive part 50 is a rectangular shape extending in the longitudinal direction of the absorbent article 1. The adhesive parts 50 are arranged side-by-side in the width direction of the absorbent article 1. The surface of the adhesive part 50 is covered with a release sheet (not shown) before use of the absorbent article 1.

Examples of the pressure-sensitive adhesive for forming the pressure-sensitive adhesive part 50 include a thermoplastic polymer such as styrene-based block polymer, a natural resin-based or synthetic resin-based tackifier resin, and a thermoplastic material such as paraffin-based oil. Examples of the styrene-based block polymer used for the pressure-sensitive adhesive part 50 include a styrene-ethylene-butadiene-styrene block copolymer (SEBS), a styrene-butadiene-styrene block copolymer (SBS), a styrene-isoprene-styrene block copolymer (SIS), and a styrene-ethylene-propylene-styrene copolymer (SEPS). Examples of the natural resin-based tackifier resin include a terpene-based resin which is a copolymer of α pinene, β pinene or dipentene, a rosin-based resin which is gum rosin, tall oil rosin or wood rosin, and a hydrogenation product or ester thereof. Examples of the synthetic resin-based tackifier resin include an aliphatic (C5-type) petroleum resin, an aromatic (C9-type) petroleum resin, a copolymerized petroleum resin, a hydrogenated petroleum resin, a DCPD-based petroleum resin, and a pure monomer-based petroleum resin. Also, the plastic material includes a paraffin oil type capable of decreasing the viscosity, a naphthene oil capable of increasing the tack, and an aromatic oil capable of decreasing the cohesive force or imparting a color or an odor.

The basis weight of the pressure-sensitive adhesive coated in the pressure-sensitive adhesive part 50 is from 10 to 100 g/m$^2$, preferably from 20 to 50 g/m$^2$. If the coated amount is less than 10 g/m$^2$, the pressure-sensitive adhesive force of the absorbent article 1 is too weak and the absorbent article 1 may not adhere to the underwear or may fall or slip during use of the absorbent article 1, giving the wearer a discomfort feeling. On the other hand, if the coated amount exceeds 100 g/m$^2$, the adhesive force of the absorbent article 1 is too strong and this may disadvantageously bring about a problem that the absorbent article 1 is ruptured when separating the absorbent article 1 from the underwear and a part of the absorbent article 1 sticks to the underwear and may not be easily removable.

The production method of the absorbent article 1 in one or more embodiments of the present invention is described below by referring to FIG. 3. In a step of producing an absorption body, a belt-like air-laid nonwoven fabric 212 is supplied from an air-laid nonwoven fabric roll 210 around which an air-laid nonwoven fabric is wound. Comminuted pulp 222 is supplied to a pattern drum 220 from a comminuted pulp supply apparatus not shown. Concave parts 224 as a mold for packing the comminuted pulp are formed in the outer circumferential part of the pattern drum 220. Suction 226 is generated on the inside of the pattern drum 220, and the comminuted pulp 222 supplied to the pattern drum 220 is sucked into the concave part 224 and compressed. The comminuted pulp layer 228 formed in the concave part 224 is stacked on the air-laid nonwoven fabric 212 and joined using a hot-melt pressure-sensitive adhesive to produce an absorption body comprising an air-laid nonwoven fabric 212 and a comminuted pulp layer 228.

Figure 4:
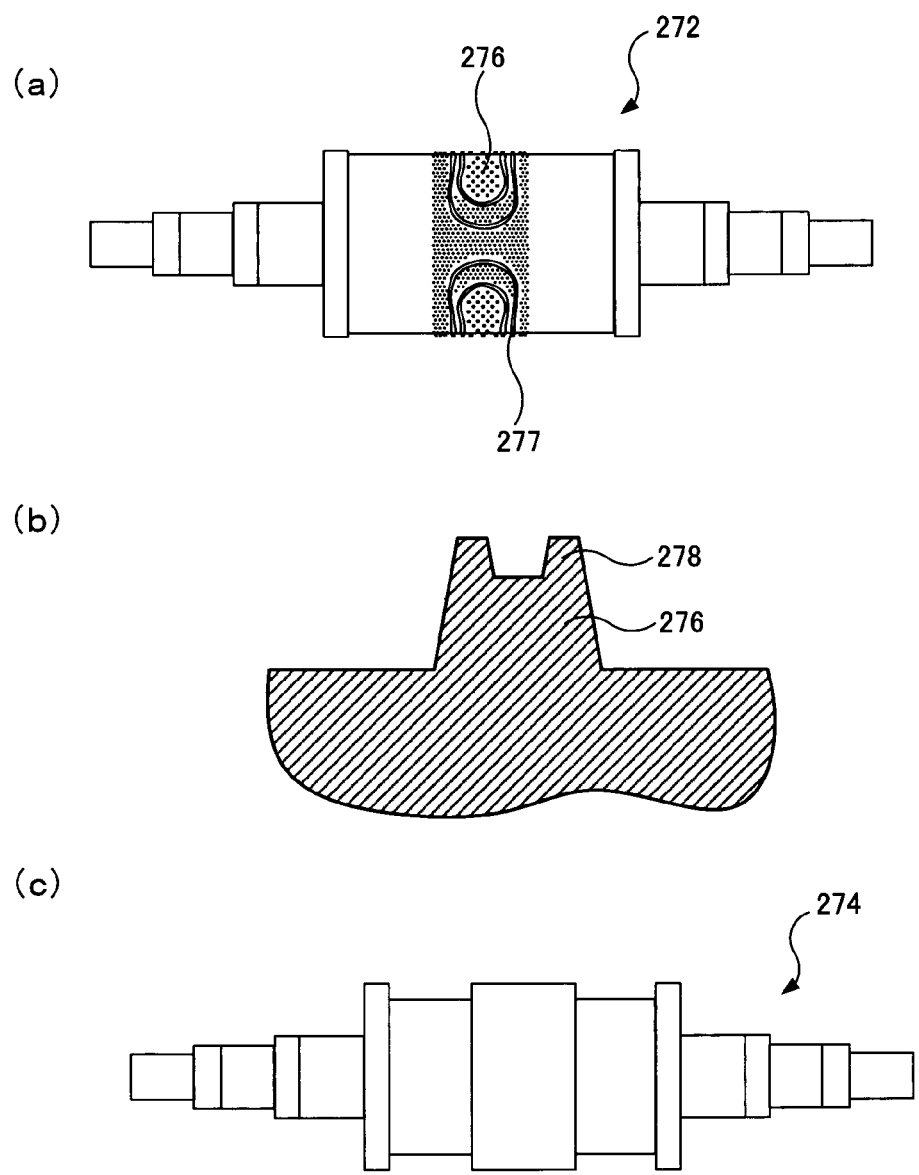
FIG. 4 is a view for explaining the upper roller and the lower roller of an embossing apparatus used at the time of producing the absorbent article in one or more embodiments of the present invention.

In a step of covering the absorption body, a surface sheet 252 supplied from a surface sheet roll 250 and a side sheet 262 supplied from a side sheet roll 260 are laminated together, and the surface sheet 252 and the side sheet 262 laminated together are disposed on the absorption body 232. In a compressed groove forming step, an absorption body 234 covered with the surface sheet 252 is compressed in the thickness direction by using an embossing apparatus 270, whereby compressed grooves and a plurality of concave parts each depressed given from the surface sheet 252 to the inside of the absorption body 234 are formed on a laminate 236 comprising the surface sheet 252, the side sheet 262 and the absorption body 234. The upper (first or second) roller 272 and the lower (second or first) roller 274 of the embossing apparatus 270 are described by referring to FIG. 4. As shown in FIG. 4(a), on the upper roller 272, pins 276 are provided at the positions corresponding to concave parts 60 and 70 provided on the absorbent article 1 (see, FIG. 1), and one or more convex parts 277 (hereinafter referred to as a ridge) for forming a compressed groove are provided at the positions corresponding to the compressed grooves 80 and 90 provided on the absorbent article 1 (see, FIG. 1). The shape of the pin 276 is a shape of truncated cone. As shown in FIG. 4(b), a protrusion 278 for forming a high compression area 62 of the concave part 60 (see, FIG. 2) is provided at the distal end of the pin 276 corresponding to the concave part 60 in the central part of the absorbent article 1. The diameter of the distal end of the pin 276 is preferably from 0.5 to 6.0 mm and in view of balance between rigidity and softness of the absorbent article 1, more preferably from 1.0 to 2.5 mm.

If the diameter of the entire distal end of the pin 276 is less than 0.5 mm, the laminate 236 may not be sufficiently compressed, whereas if it exceeds 6.0 mm, the laminate 236 may be too much compressed to give an excessively hard laminate 236. The width of the ridge 277 is preferably from 1 to 6.0 mm, more preferably from 2 to 3 mm. If the width of the ridge is less than 1 mm, the surface sheet 252 may be ruptured along the ridge 277, whereas if it exceeds 6 mm, the laminate 236 may become excessively hard. As shown in FIG. 4(c), a protrusion such as pin is not formed on the lower roller 274.

The plurality of concave parts and the compressed grooves are simultaneously formed by passing the absorption body 234 covered with the surface sheet 252 between the upper roller 272 having pins 276 and ridges 277 and the lower roller 274 disposed to face the upper roller 272, so that positioning of the compressed grooves with respect to the plurality of concave parts is facilitated as compared with the case of separately forming the plurality of concave parts and the compressed grooves, and also, the production process of the absorbent article can be simplified. Furthermore, the density in the portion of the uncompressed region of the absorption body is increased every time the absorption body passes between the upper roller and the lower roller and in the case of separately forming the plurality of concave parts and the compressed grooves, the absorption body passes through the upper roller and the lower roller one extra time, as a result, the density in the portion of the uncompressed region of the absorption body is increased. However, since the plurality of concave parts and the compressed grooves are simultaneously formed, the density in the portion of the uncompressed region of the absorption body can be kept from increasing. In turn, the difference between the density in the portion of the concave part or compressed groove of the absorption body and the density in the portion of the uncompressed region of the absorption body can be made large, and the effect of preventing the body fluid of the wearer from diffusing to the end of the absorbent article is increased.

Figure 3:
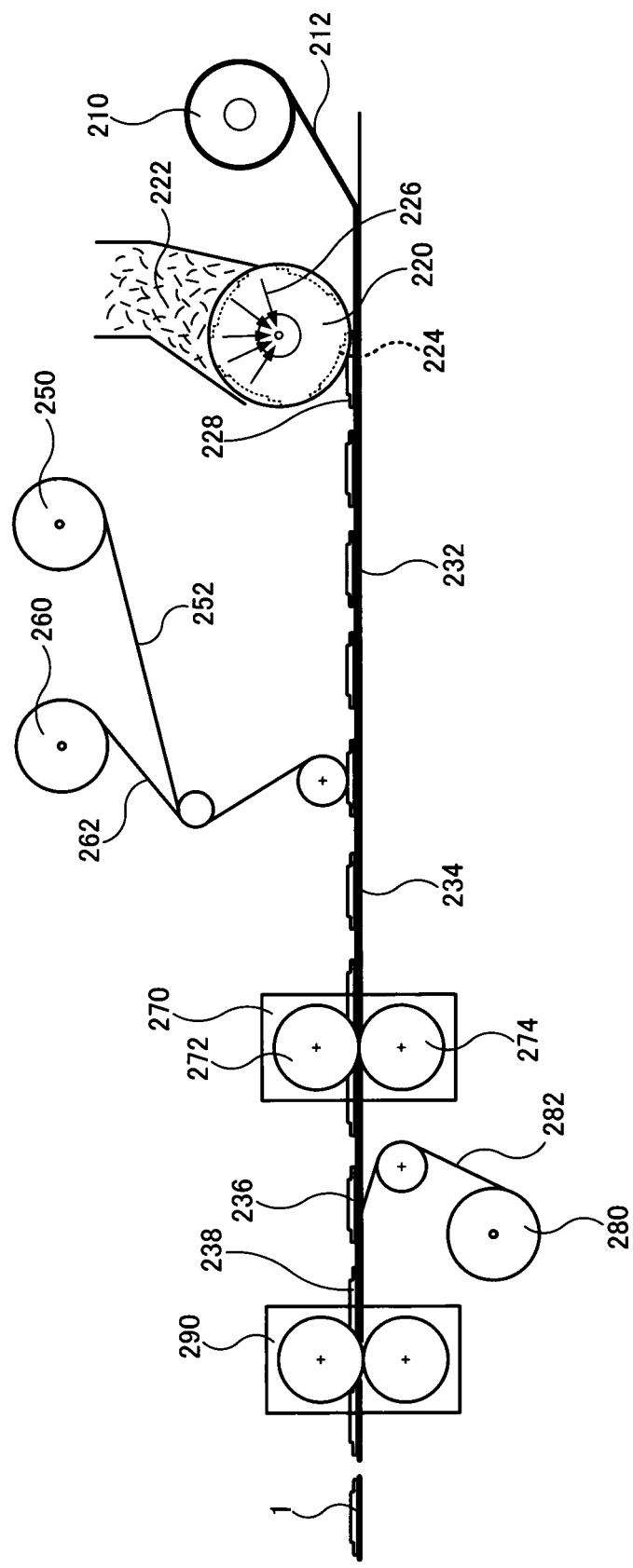
FIG. 3 is a view for explaining the production method of the absorbent article in one or more embodiments of the present invention.

A backside sheet 282 supplied from the backside sheet roll 280 shown in FIG. 3 is superposed on and bonded to the embossed laminate 236 on the surface opposite to the surface sheet 252 to form a continuous body 238 of absorbent article, and the continuous body 238 of absorbent article is cut into an absorbent article shape by using a cutter 290, whereby an absorbent article 1 is produced.

The above-described absorbent article 1 in one or more embodiments of the present invention can be modified as follows.

Figure 5:
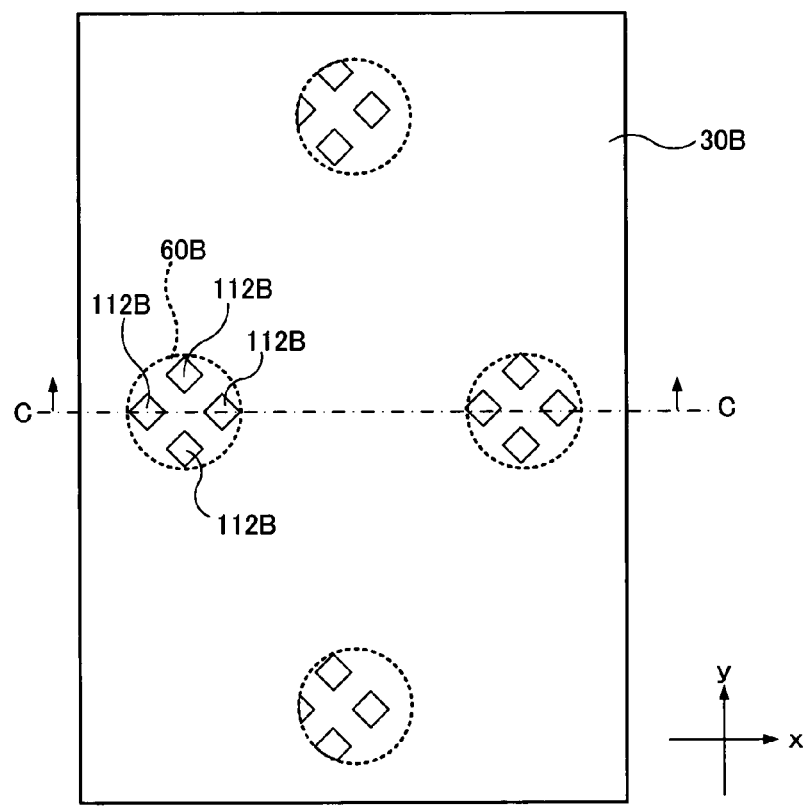
FIG. 5 is a view for explaining the high compression area and the low compression area provided in a modified example of the absorbent article in one or more embodiments of the present invention.
Figure 5:
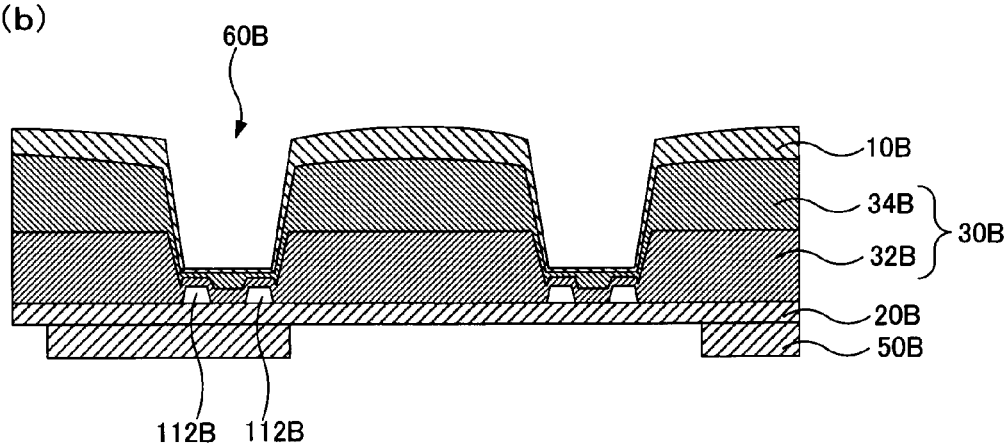

(1) In the absorbent article 1 above, a high compression area 62 and a low compression area 64 differing in the depth in the thickness direction are provided at least in concave parts 60 of the plurality of concave parts 60 and 70. However, as shown in FIG. 5, a plurality of compressed parts 112B may be provided at the positions opposing the plurality of concave parts 60B on the non-skin-facing side of the absorption body 30B. FIG. 5(a) is a plan view of the compressed part 112B, and FIG. 5(b) is a C-C cross-sectional view of FIG. 5(a). As a result, a coarse-dense gradient of the absorption body 30B is created in the bottom of the concave part 60B, and absorption of the body fluid of the wearer by the absorbent article is improved. Also, the inside surface of the concave part 60B has no unevenness and therefore, even a highly viscous body fluid of the wearer can be successfully absorbed. Incidentally, it is also possible to provide a compressed part 112B partially overlapping a corresponding concave part 60B on the non-skin-facing side of the absorption body 30B.

Figure 6:
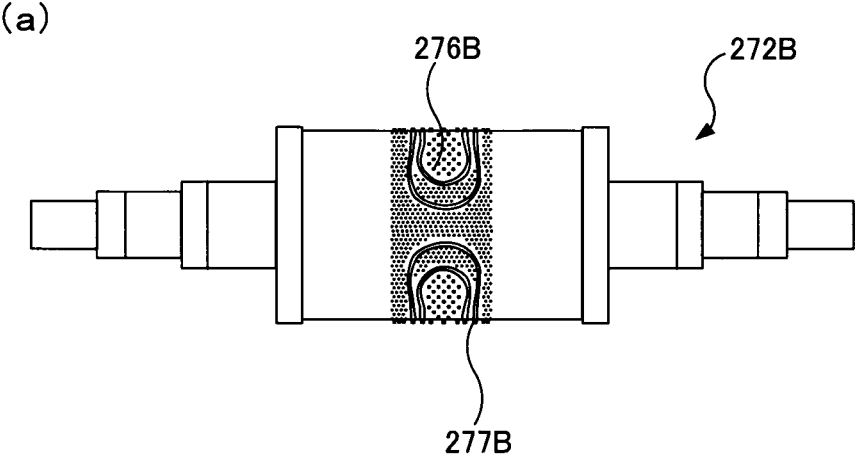
FIG. 6 is a view for explaining the upper roller of an embossing apparatus used for forming the concave part provided in a modified example of the absorbent article in one or more embodiments of the present invention.
Figure 6:
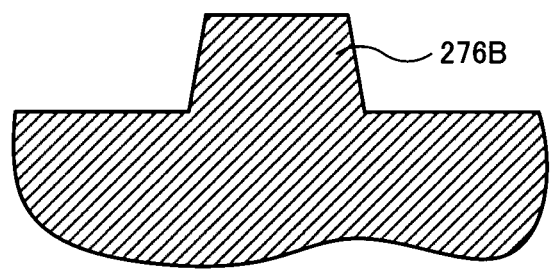
Figure 7:
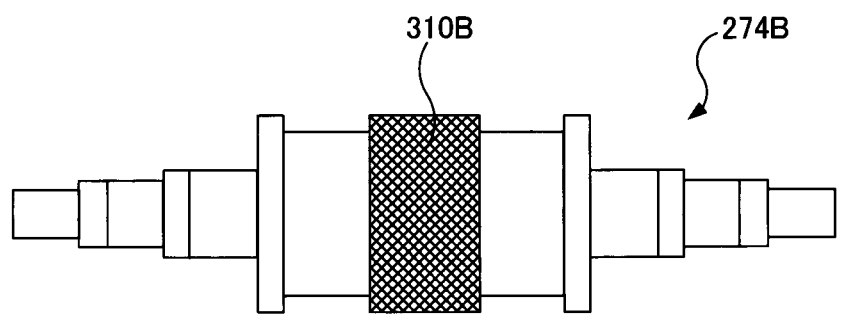
FIG. 7 is a view for explaining the lower roller of an embossing apparatus used for forming the high compression area and the low compression area provided in a modified example of the absorbent article in one or more embodiments of the present invention.
Figure 7:
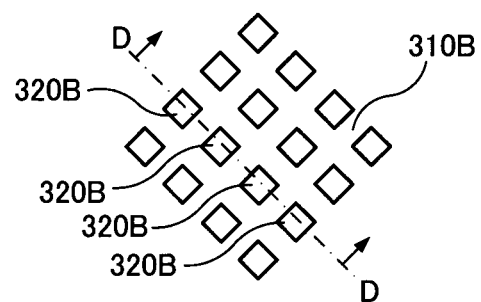
Figure 7:
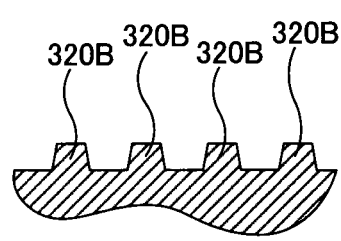

The upper roller and the lower roller of the embossing apparatus for forming the concave part 60B on the surface sheet 10B and the absorption body 30B and forming the compressed part 112B on the absorption body 30B are described by referring to FIGS. 6 and 7. FIG. 6(a) is a view showing the upper roller, and FIG. 6(b) is a cross-sectional view of the pin provided on the upper roller. As shown in FIG. 6(a), in the upper roller 272B, pins 276B are provided at the positions corresponding to the concave parts provided on the absorbent article, and ridges 277B are provided at the positions corresponding to the compressed grooves provided on the absorbent article. As shown in FIG. 6(b), the shape of the pin is a shape of a truncated cone. Unlike the upper roller 272 of the embossing apparatus 270 used for the absorbent article 1 above, a protrusion 278 for forming a high compression area of the concave part is not provided at the distal end of the pin.

FIG. 7(a) is a view showing the lower roller, FIG. 7(b) is an enlarged view showing grid-like grooves provided on the lower roller, and FIG. 7(c) is a D-D cross-sectional view of FIG. 7(b). As shown in FIG. 7(a), grid-like grooves 310B are provided on the lower roller 274B. As shown in FIGS. 7(b) and 7(c), protrusions 320B having a shape of a truncated pyramid with a square-shaped top are formed by the grid-like grooves 310B on the lower (second) roller. Compared with the protrusion 278 provided at the distal end of the pin on the upper roller 272 of the embossing apparatus 270 used for the absorbent article 1, the protrusion 320B are evenly provided on the lower roller 274B and less likely to be chipped or shaved. Incidentally, it is also possible to form the compressed part by using a lower roller having uniformly provided thereon protrusions whose planewise cross-section has a circular shape or a polygonal shape other than the square.

Figure 8:
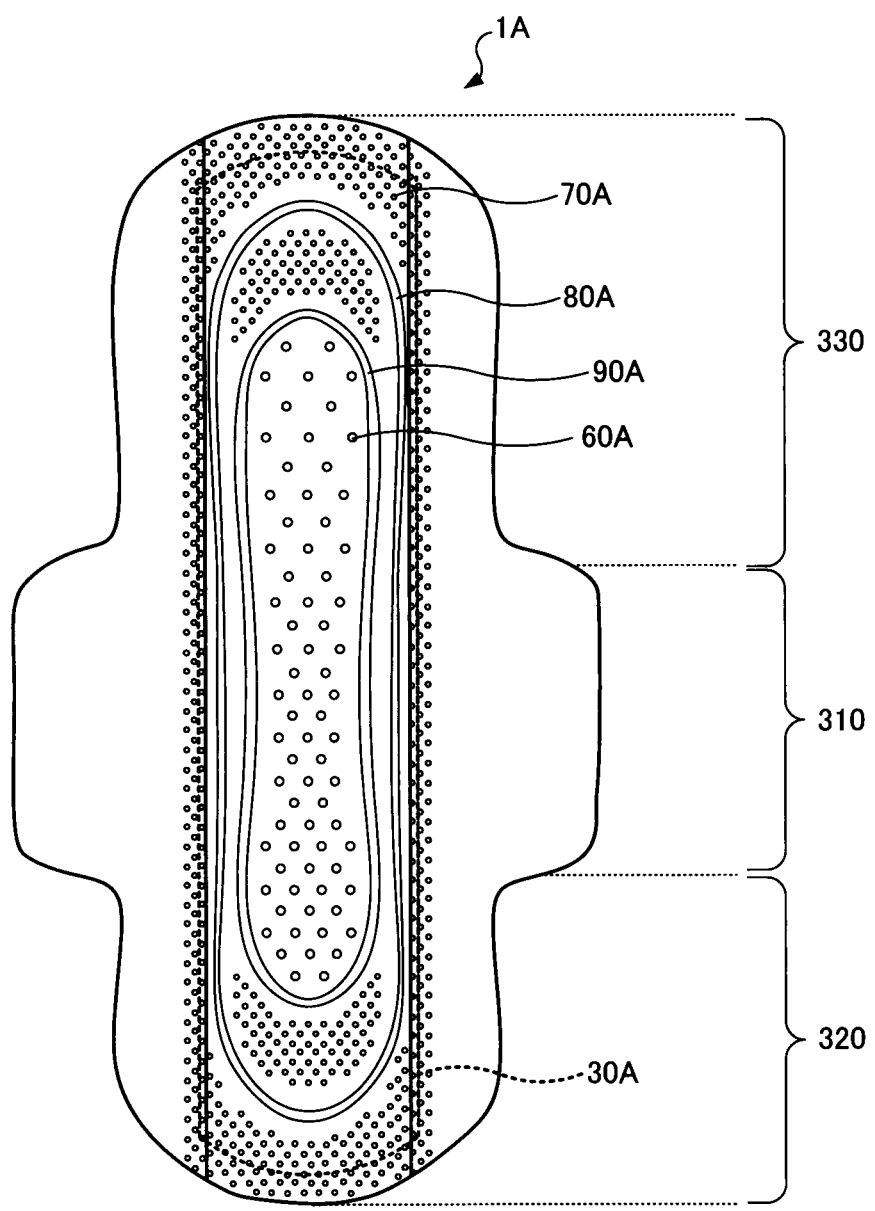
FIG. 8 is a view for explaining a modified example of the absorbent article in one or more embodiments of the present invention.

(2) The above-described absorbent article 1 in one or more embodiments may be a sanitary napkin extending into the buttocks of the wearer, for example, a nighttime sanitary napkin 1A worn during sleep. As shown in FIG. 8, the sanitary napkin 1A has a crotch zone 310 to be applied to the crotch part of the wearer, a front waist zone 320 for covering the front side relative to the crotch part of the wearer, and a rear waist zone 330 for covering the rear side relative to the crotch part of the wearer. Also, as shown in FIG. 8, the sanitary napkin 1A has an outer first compressed groove 80A, an inner second compressed groove 90A, a plurality of concave parts 70A provided outside the inner second compressed groove 90A, and a plurality of concave parts 60A provided inside the inner second compressed groove 90A, and has an absorption body 30A in the inside. The inner second compressed groove 90A is provided to extend from the crotch zone 310 to the rear waist zone 330, and the plurality of concave parts 60A inside the inner second compressed groove 90A is provided in the crotch zone 310 and the rear waist zone 330. As shown in FIG. 8, the number per unit area of concave parts 60A provided in the crotch zone 310 is larger than the number per unit area of concave parts 60A provided in the rear waist zone 330. Thanks to this configuration, the density in the portion of the crotch zone 310 inside the inner second compressed groove 90A of the absorption body 30A becomes higher than the density in the portion of the rear waist zone 330 inside the inner second compressed groove 90A of the absorption body 30A, so that the body fluid discharged from the wearer can be prevented from diffusing to the rear waist zone 330. Incidentally, the number per unit area of concave parts 60A inside the inner second compressed groove 90A of the absorption body 30A may be arranged to gradually decrease along the way from the front waist side 320 to the rear waist zone 330.

(3) The above-described absorbent article 1 in one or more embodiments is a sanitary napkin, but further embodiments of the present invention can also be applied to other absorbent articles such as a pantiliner, incontinence pad and incontinence liner. Embodiments of the present invention are suitable particularly thin absorbent articles, for example, an absorbent article having thickness of less than 4 mm.

EXAMPLES (Diffusion Test with Artificial Menstrual Blood)

Figure 9:
FIG. 9 is a photograph showing how the artificial menstrual blood diffuses on the widthwise side of the absorbent article in one or more embodiments of the present invention.
Figure 9:
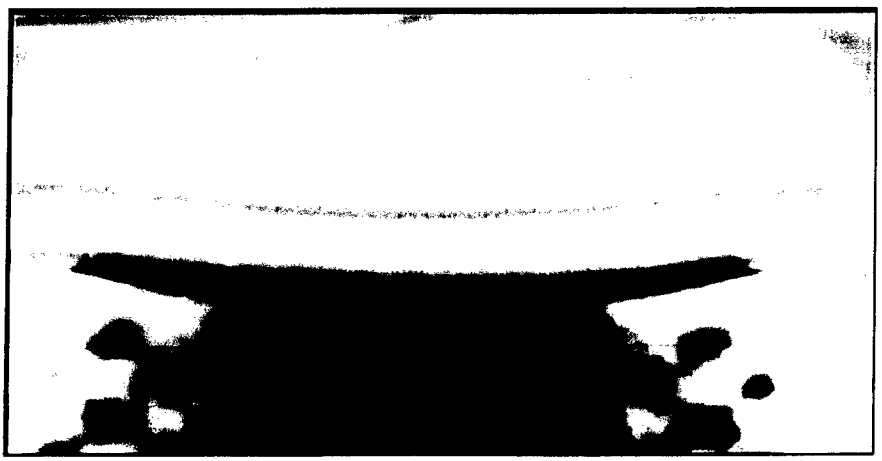

Artificial menstrual blood (3 ml) was dropped at a rate of 10 ml/min on an absorbent article having an uncompressed region, and the diffusion state of menstrual blood was checked after 1 minute and after 5 minutes. The width of the uncompressed region was 6 mm. FIG. 9 shows how the artificial menstrual blood diffuses on the widthwise side of the absorbent article. FIG. 9(a) is a photograph showing the diffusion state 1 minute after the dropping of artificial menstrual blood, and FIG. 9(b) is a photograph showing the diffusion state 5 minutes after the dropping of artificial menstrual blood. It is seen from these photographs that the artificial menstrual blood stopped at the inner compressed groove even after the passing of 5 minutes.

Figure 10:
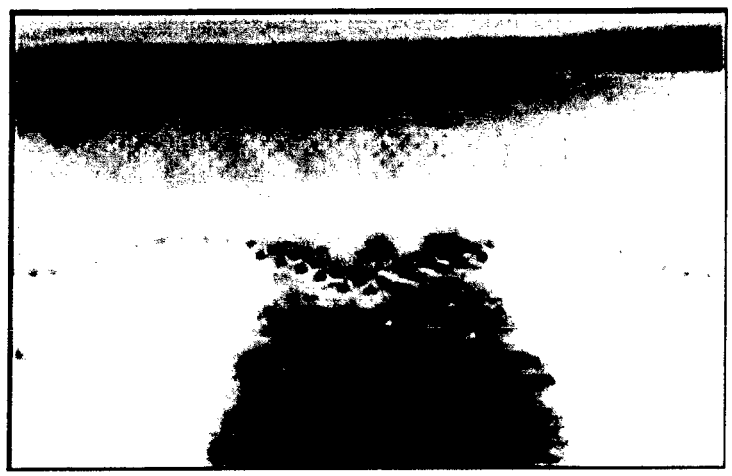
FIG. 10 is a photograph showing how the artificial menstrual blood diffuses on the widthwise side of an absorbent article where an uncompressed region is substantially absent.
Figure 10:

For comparison, an absorbent article where the concave parts are provided even in the vicinity of the compressed groove, and an uncompressed region is substantially absent was also checked for the diffusion state of the artificial menstrual blood. FIG. 10 shows how the artificial menstrual blood diffuses on the widthwise side of an absorbent article where an uncompressed region is substantially absent. FIG. 10(a) is a photograph showing the diffusion state 1 minute after the dropping of the artificial menstrual blood, and FIG. 10(b) is a photograph showing the diffusion state 5 minutes after the dropping of the artificial menstrual blood. It is seen from these photographs that the artificial menstrual blood passed through the inner compressed groove 5 minutes after the dropping of the artificial menstrual brood.

The artificial menstrual blood was produced as follows.

In Plastic Container A, 320±2 g of glycerin (produced by Wako Pure Chemical Industries, Ltd., Wako first class) was charged and after further adding 32.0±0.3 g of sodium carboxymethyl cellulose (NaCMC) (produced by Wako Pure Chemical Industries, Ltd., chemical), the mixture was stirred for 10 minutes at a rotation speed of about 600 rpm by a stirrer to produce Solution A. Solution A prepared above was added little by little to 3 liters of ion-exchanged water charged in another Polyester Container B, with stirring at a rotation speed of about 1,100 rpm by a stirrer (manufactured by HSIANGTAI MACHINERY INDUSTRY CO., LTD.). Furthermore, 1 liter of ion-exchanged water was added while washing Plastic Container A. To the thus-obtained Solution B, 40 g of sodium chloride (NaCl) (produced by Wako Pure Chemical Industries, Ltd., guaranteed reagent) and 16 g of sodium hydrogencarbonate ($NaHCO_3$) (produced by Wako Pure Chemical Industries, Ltd., Wako first class) were added little by little with stirring, and after the completion of addition, the mixture was stirred for about 3 hours. Subsequently, food dye preparations (produced by Koyo Produck Co., Ltd.), that is, 32 g of Red No. 102, 8 g of Red No. 2 and 8 g of Yellow No. 5, were added with stirring to Solution C obtained by the preparation above, and the mixture was then stirred for about 1 hour to obtain artificial menstrual blood. The viscosity of the obtained artificial menstrual blood was measured by a viscometer (Vismetron Model VGA-4, manufactured by Shibaura Systems Co., Ltd.) and found to be from 22 to 26 mPa·s.

(Relationship Between Diffusion of Artificial Menstrual Blood and Density of Absorption Body)

The diffusion state of artificial menstrual blood in the absorbent article was exampled by varying the difference between the density in the portion of the uncompressed region of the absorption body and the density in the portion having formed therein a compressed groove of the absorption body. The density of the absorption body was measured as follow. The absorbent article was frozen by impregnating it with liquid nitrogen and cut with a razor and, after returning to ordinary temperature, the thickness of the absorption body was measured using an electron microscope (for example, VE7800 of Keyence) at a magnification of 50 times. The reason why the absorbent article was frozen is because the thickness can be prevented from fluctuation due to compression during cutting with a razor. The basis weight of the absorption body before use was divided by the thickness to calculate the density.

Figure 11:
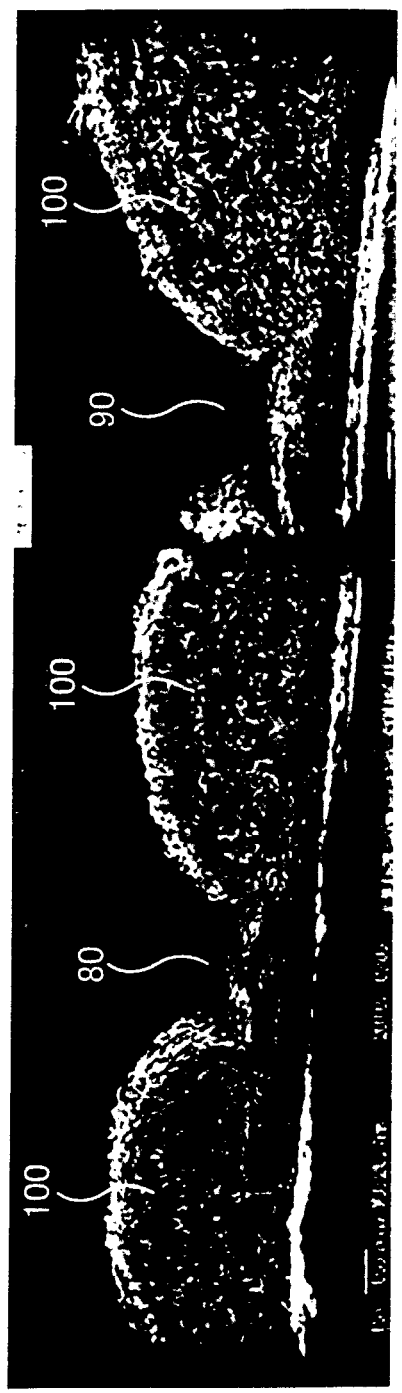
FIG. 11 is a photograph taken to measure the density of the absorption body of the absorbent article in one or more embodiments of the present invention.

FIG. 11 shows one example of the electron micrograph of the cross-section of the absorbent article. In the electron micrograph of FIG. 11, the outer first compressed groove 80, the inner second compressed groove 90 and the uncompressed region 100 are shown. In the absorption body shown in FIG. 11, the thickness in the portion of the uncompressed region 100 outside the outer first compressed groove 80 was 2.31 mm, the thickness in the portion of the outer first compressed groove 80 was 0.50 mm, the thickness in the portion of the uncompressed region 100 between the outer first compressed groove 80 and the inner second compressed groove 90 was 2.65 mm, the thickness in the portion of the inner second compressed groove 90 was 0.48 mm, and the thickness in the portion of the uncompressed region 100 inside the inner second compressed groove 90 was 3.75 mm. Also, on the longitudinal side (not shown) of the absorbent article, the thickness in the portion of the uncompressed region outside the outer compressed groove 80 of the absorption body was 1.85 mm, the thickness in the portion of the outer first compressed groove 80 was 0.29 mm, the thickness in the portion of the uncompressed region between the outer first compressed groove 80 and the inner second compressed groove 90 was 1.55 mm, the thickness in the portion of the inner second compressed groove 90 was 0.29 mm, and the thickness in the portion of the uncompressed region 100 inside the inner second compressed groove 90 was 3.09 mm. The basis weight of the pulp layer as the upper layer of the absorption body was 100 g/m$^2$, and the basis weight of the air-laid layer as the lower layer of the absorption body was 50 g/m$^2$.

The density at each portion calculated from the thickness measured above and the basis weights of the pulp layer and the air-laid layer was as follows. In the absorption body shown in FIG. 11, the density in the portion of the uncompressed region 100 outside the outer first compressed groove 80 was 0.065 g/cm$^3$, the density in the portion of the outer first compressed groove 80 was 0.3 g/cm$^3$, the density in the portion of the uncompressed region 100 between the outer first compressed groove 80 and the inner second compressed groove 90 was 0.057 g/cm$^3$, the density in the portion of the inner second compressed groove 90 was 0.31 g/cm$^3$, and the density in the portion of the uncompressed region 100 inside the inner second compressed groove 90 was 0.04 g/cm$^3$. Also, on the longitudinal side (not shown) of the absorbent article, the density in the portion of the uncompressed region outside the outer compressed groove of the absorption body was 0.081 g/cm$^3$, the density in the portion of the outer first compressed groove 80 was 0.52 g/cm$^3$, the density in the portion of the uncompressed region between the outer first compressed groove 80 and the inner second compressed groove 90 was 0.097 g/cm$^3$, the density in the portion of the inner second compressed groove 90 was 0.52 g/cm$^3$, and the density in the portion of the uncompressed region 100 inside the inner second compressed groove 90 was 0.049 g/cm$^3$. Even when 3 ml of artificial menstrual blood was dropped on this absorbent article, the artificial menstrual blood did not diffuse to the outside of the outer first compressed groove 80.

Figure 12:
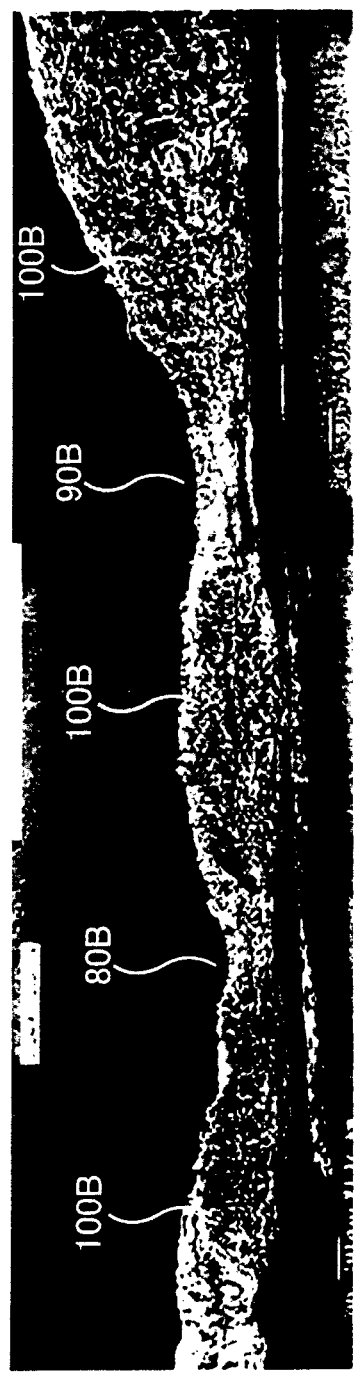
FIG. 12 is a photograph taken to measure the density of the absorption body of an absorbent article where the difference between the density in the portion of the compressed groove of the absorption body and the density in the portion of the uncompressed region of the absorption body is reduced.

Next, an absorbent article with a reduced difference between the density in the portion of the compressed groove 80B/90B of the absorption body and the density in the portion of the uncompressed region 100B of the absorption body was produced to examine whether or not the artificial menstrual blood diffuses over the first compressed groove 80 when the density difference becomes small. The electron micrograph of FIG. 12 is a photograph of the cross-section of the absorbent article with such a reduced density difference, and the outer first compressed groove 80B, the inner second compressed groove 90B and the uncompressed region 100B are shown. In the absorption body shown in FIG. 12, the thickness in the portion of the uncompressed region 100B outside the outer first compressed groove 80B was 0.85 mm, the thickness in the portion of the outer first compressed groove 80B was 0.63 mm, the thickness in the portion of the uncompressed region 100B between the outer first compressed groove 80B and the inner second compressed groove 90B was 1.13 mm, the thickness in the portion of the inner second compressed groove 90B was 0.43 mm, and the thickness in the portion of the uncompressed region 100B inside the inner second compressed groove 90B was 2.66 mm. Also, on the longitudinal side (not shown) of the absorbent article, the thickness in the portion of the uncompressed region outside the compressed groove 80B, 90B of the absorption body was 1.12 mm, the thickness in the portion of the compressed groove 80B, 90B was 0.35 mm, and the thickness in the portion of the uncompressed region inside the compressed groove 80B, 90B was 0.93 mm. The basis weight of the pulp layer as the upper layer of the absorption body was 100 g/m$^2$, and the basis weight of the air-laid layer as the lower layer of the absorption body was 50 g/m$^2$.

The density at each portion calculated from the thickness measured above and the basis weights of the pulp layer and the air-laid layer was as follows. In the absorption body shown in FIG. 12, the density in the portion of the uncompressed region 100B outside the outer first compressed groove 80B was 0.18 g/cm$^3$, the density in the portion of the outer first compressed groove 80B was 0.24 g/cm$^3$, the density in the portion of the uncompressed region 100B between the outer first compressed groove 80B and the inner second compressed groove 90B was 0.13 g/cm$^3$, the density in the portion of the inner second compressed groove 90B was 0.35 g/cm$^3$, and the density in the portion of the uncompressed region 100B inside the inner second compressed groove 90B was 0.06 g/m$^3$. Also, on the longitudinal side of the absorbent article, the density in the portion of the uncompressed region outside the compressed groove 80B, 90B of the absorption body was 0.13 g/cm$^3$, the density in the portion of the compressed groove 80B, 90B was 0.43 g/cm$^3$, and the density in the portion of the uncompressed region inside the compressed groove 80B, 90B was 0.16 g/cm$^3$. When 3 ml of artificial menstrual blood was dropped on this absorbent article, the artificial menstrual blood diffused to the outside of the first compressed groove 80.

These results reveal that for effectively preventing the body fluid of the wearer from diffusing to the end of the absorbent article 1, the density in the portion of the uncompressed region 100 of the absorption body 30 is preferably ¼ or less of the density in the portion having formed therein the compressed groove 80 or 90 of the absorption body 30. That is, the thickness in the portion of the uncompressed region 100 of the absorption body 30 is revealed to be preferably 4 times or more of the thickness in the portion having formed therein the compressed groove 80 or 90 of the absorption body 30.

One or more embodiments and/or one or more modification examples may be combined in any combination.

The description above has been provided as examples only, and the present invention is not limited to the above-described embodiments.

This application claims the benefit of Japanese Application No. 2011-044959 the entire disclosure of which is incorporated by reference therein.

DESCRIPTION OF NUMERICAL REFERENCES

1 Absorbent article
10 Surface sheet
20 Backside sheet
30 Absorption body
32 Air-laid layer
34 Comminuted pulp layer
40 Side sheet
50 Pressure-sensitive adhesive part
60, 70 Concave part
62 High compression area
64 Low compression area
80, 90 Compressed groove
100 Uncompressed region
210 Air-laid nonwoven roll
220 Pattern drum
250 Surface sheet roll
260 Side sheet roll
270 Embossing apparatus
272 Upper roller
274 Lower roller
276 Pin
277 Ridge
280 Backside sheet roll
290 Cutter

The invention claimed is:
1. An absorbent article, comprising:
a liquid-pervious surface sheet,
a liquid-impervious backside sheet opposing said surface sheet in a thickness direction of the absorbent article,
an absorption body provided between said surface sheet and said backside sheet,
an endless compressed groove surrounding a central part of said absorbent article and formed in said surface sheet and said absorption body in the thickness direction,
a plurality of concave parts provided in the central part and outside the central part of the absorbent article, said plurality of concave parts being formed in said surface sheet and said absorption body in the thickness direction, and
an uncompressed region bordering inner and outer edges of the compressed groove, wherein
a closest distance between said compressed groove and a nearest concave part is greater than a distance between closest adjacent concave parts among the plurality of concave parts.
2. The absorbent article as claimed in claim 1, wherein the closest distance between said compressed groove and the nearest concave parts in the central part of said absorbent article is greater than the distance between closest adjacent concave parts among the concave parts in the central part of the absorbent article.
3. The absorbent article as claimed in claim 1, wherein the closest distance between said compressed groove and the nearest concave parts outside the central part of the absorbent article is greater than the distance between closest adjacent concave parts among the concave parts outside the central part of the absorbent article.
4. The absorbent article as claimed in claim 1, wherein said groove is circular or oval in shape.
5. The absorbent article as claimed in claim 1, wherein said absorption body includes a comminuted pulp layer and an air-laid layer formed of fibers joined together with a binder,
said comminuted pulp layer is provided on a skin-facing side of said absorption body,
said air-laid layer is provided on a non-skin-facing side of said absorption body,
an area of the air-laid layer is greater than an area of the comminuted pulp layer, and the comminuted pulp layer overlies the air-laid layer so that the air-laid layer encompasses the comminuted pulp layer in a plane of the absorption body, and
a longitudinal end part of said comminuted pulp layer is present on an outer side of said uncompressed region bordering the outer edge of the said compressed groove.
6. The absorbent article as claimed in claim 1 having an elongated shape with a greater longitudinal length than transverse width,
wherein a width of the uncompressed region towards a transverse side of said absorbent article is greater than a width of the same uncompressed region towards a longitudinal end of said absorbent article.
7. The absorbent article as claimed in claim 1, wherein a width of the uncompressed region bordering the outer edge of said compressed groove is larger than a width of the uncompressed region bordering the inner edge of said compressed groove.
8. The absorbent article as claimed in claim 1, wherein said compressed groove is a first compressed groove,
the absorbent article further comprises a second compressed groove surrounding the central part of said absorbent article, and compressed in said surface sheet and said absorption body in the thickness direction, and said second compressed groove is provided on an outer side of said first compressed groove,
said plurality of concave parts are also disposed between said first compressed groove and said second compressed groove, and
said uncompressed region includes uncompressed regions present between said first compressed groove and said second compressed groove.
9. The absorbent article as claimed in claim 8, wherein said concave parts are not provided between said first compressed groove and said second compressed groove on transverse sides of said absorbent article.
10. The absorbent article as claimed in claim 8, further comprising:
a crotch zone configured to be applied to a crotch region of a wearer, and
a rear waist zone configured to cover a rear side region of the wearer relative to the crotch part of the wearer, wherein
said second compressed groove is provided from the crotch zone to the rear waist zone,
said plurality of concave parts in the central part of the absorbent article is provided in said crotch zone and said rear waist zone, and
a number per unit area of said concave parts provided in said crotch zone is larger than a number per unit area of said concave parts provided in said rear waist zone.
11. The absorbent article as claimed in claim 8, wherein a closest distance between the first and second compressed grooves is larger than a distance between closest adjacent concave parts among the concave parts that are present outside the central part of the absorbent article.
12. The absorbent article as claimed in claim 8, wherein a density of the absorption body in the uncompressed region is ¼ or less of a density of the absorption body in the first compressed groove, the second compressed groove, or the concave parts.

13. The absorbent article as claimed in claim 8, wherein a thickness of the absorption body in the uncompressed region is 4 times or more of the thickness of the absorption body in the first compressed groove, the second compressed groove, or the concave parts.

14. The absorbent article as claimed in claim 1, wherein the central part is configured to be arranged in a crotch region of a wearer.

15. The absorbent article as claimed in claim 1 in a form of a sanitary napkin, pantiliner, incontinence pad or incontinence liner, having a maximum thickness of 4 mm.

16. The absorbent article as claimed in claim 1, wherein said compressed groove is a first compressed groove,
the absorbent article further comprises: a second compressed groove defining a continuous or discontinuous loop surrounding the central part of said absorbent article and compressed in said surface sheet and said absorption body in the thickness direction, and the second compressed groove is provided on an outer side of said first compressed groove,
said concave parts are also disposed between said first compressed groove and said second compressed groove, and
the uncompressed region includes uncompressed regions present between said first compressed groove and said second compressed groove.

17. The absorbent article as claimed in claim 1, wherein in a plan view, a size of the concave parts in the central part of the absorbent article is larger than a size of the concave parts outside the central part of the absorbent article.

18. The absorbent article as claimed in claim 1, wherein a number of concave parts per unit area in the central part of the absorbent article is smaller than a number of concave parts per unit area outside the central part of the absorbent article.

19. The absorbent article as claimed in claim 1, wherein
said absorption body includes a comminuted pulp layer and an air-laid layer formed of fibers joined together with a binder,
said comminuted pulp layer is provided on a skin-facing side of said absorption body,
said air-laid layer is provided on a non-skin-facing side of said absorption body,
said compressed groove is a first compressed groove,
the absorbent article further comprises a second compressed groove surrounding the central part of said absorbent article, and compressed in said surface sheet and said absorption body in the thickness direction, and said second compressed groove is provided on an outer side of said first compressed groove, and
a longitudinal end part of said comminuted pulp layer is present on the outer side of said uncompressed region bordering the outer edge of the said second compressed groove.

20. The absorbent article as claimed in claim 1, wherein
said compressed groove is a first compressed groove, the absorbent article further comprising a second compressed groove surrounding the central part of said absorbent article and compressed in said surface sheet and said absorption body in the thickness direction, and said second compressed groove is provided on an outer side of said first compressed groove,
the uncompressed region also borders inner and outer edges of the second compressed groove.

21. An absorbent article, comprising:
a liquid-pervious surface sheet,
a liquid-impervious backside sheet opposing said surface sheet in a thickness direction of the absorbent article,
an absorption body provided between said surface sheet and said backside sheet,
a compressed groove defining a loop surrounding a central part of said absorbent article, and compressed in said surface sheet and said absorption body in the thickness direction, and
a plurality of concave parts pin embossed in said surface sheet and said absorption body in the thickness direction, and
an uncompressed region present in the central part and outside the central part of the absorbent article and along said compressed groove, and
wherein a closest distance between said compressed groove and said concave parts is larger than a distance between closest adjacent concave parts among said concave parts.

22. A method of producing an absorbent article including
a liquid-pervious surface sheet,
a liquid-impervious backside sheet opposing said surface sheet in a thickness direction of the absorbent article,
an absorption body provided between said surface sheet and said backside sheet,
an endless compressed groove surrounding a central part of said absorbent article and formed in said surface sheet and said absorption body in the thickness direction,
a plurality of concave parts provided in the central part and outside the central part of the absorbent article, said plurality of concave parts being formed in said surface sheet and said absorption body in the thickness direction, and
an uncompressed region bordering inner and outer edges of the compressed groove, wherein
a closest distance between said compressed groove and a nearest concave part is greater than a distance between closest adjacent concave parts among the plurality of concave parts, said method comprising:
producing the absorption body,
covering said absorption body with the surface sheet, and
passing said absorption body covered with said surface sheet between (i) a first roller equipped with a convex part for forming a compressed groove and pins for pin embossing and (ii) a second roller to form
the compressed groove resulting from compression of said surface sheet and said absorption body in the thickness direction with said convex part, and
the plurality of concave parts resulting from compression of said surface sheet and said absorption body in the thickness direction by pin embossing with said pins.

23. The method as claimed in claim 22, wherein
a protrusion is provided at a distal end of each pin and forms a high compression area in the concave part corresponding to said pin.

24. The method as claimed in claim 22, wherein
a plurality of protrusions is provided on the second roller and forms a plurality of compressed parts provided at positions opposing the plurality of concave parts on a non-skin-facing side of the absorption body.

25. A method of producing the absorbent article of claim 1, comprising:
producing the absorption body,
covering said absorption body with the surface sheet, and passing said absorption body covered with said surface sheet between (i) an upper roller equipped with a convex part for forming a compressed groove and pins for pin embossing and (ii) a lower roller located to face said upper roller to form the compressed groove resulting from compression of said surface sheet and said absorption body in the thickness direction and the plurality of concave parts resulting from compression of said surface sheet and said absorption body in the thickness direction by pin embossing.

\* \* \* \* \*